US005610023A

United States Patent [19]

Deutsch

[11] Patent Number: 5,610,023

[45] Date of Patent: Mar. 11, 1997

[54] METHOD OF PURIFICATION OF CLOSTRIDIUM DIFFICILE TOXIN A AND PRODUCTION OF MONO-SPECIFIC ANTIBODIES

[75] Inventor: John W. Deutsch, Marietta, Ga.

[73] Assignee: Lee Laboratories, Inc., Grayson, Ga.

[21] Appl. No.: 414,640

[22] Filed: Mar. 31, 1995

[51] Int. Cl.[6] ........................ G01N 33/554; G01N 33/569

[52] U.S. Cl. ........................... 435/7.32; 435/7.2; 436/533

[58] Field of Search .............................. 436/533; 435/7.2, 435/240.27, 6, 240, 7.32, 842, 828

[56] References Cited

U.S. PATENT DOCUMENTS

| | | | |
|---|---|---|---|
| 4,530,833 | 7/1985 | Wilkins et al. | 424/92 |
| 4,533,630 | 8/1985 | Wilkins et al. | 435/7 |
| 4,563,419 | 1/1986 | Ranki et al. | 435/6 |
| 4,689,299 | 8/1987 | Insel et al. | 435/240.27 |
| 4,863,852 | 9/1989 | Wilkins et al. | 435/7 |
| 4,879,218 | 11/1989 | Wilkins et al. | 435/7 |
| 4,937,201 | 6/1990 | Ueno et al. | 436/533 |
| 4,959,457 | 9/1990 | Bringman | 530/387 |
| 5,071,759 | 12/1991 | Rothman et al. | 435/240.27 |
| 5,098,826 | 3/1992 | Wilkins et al. | 435/7.32 |
| 5,231,003 | 7/1993 | Coughlin et al. | 435/7.32 |
| 5,266,315 | 11/1993 | Taguchi et al. | 424/93 |
| 5,316,911 | 5/1994 | Baek et al. | 435/7.9 |
| 5,545,721 | 8/1996 | Carroll et al. | 530/391.7 |

FOREIGN PATENT DOCUMENTS

| | | | |
|---|---|---|---|
| 84301395 | 3/1984 | European Pat. Off. | C12P 1/04 |
| 84301394 | 3/1984 | European Pat. Off. | C07K 15/06 |

OTHER PUBLICATIONS

Lyerly et al., Monoclonal and Specific Polyclonal Antibodies for Immunoassay of C. difficile Toxin A, Jrnl. of Clinical Microbiology, Jan. 1985, p. 12–14.

Domen et al., Site-directed immobilization of proteins, Jrnl. of Chromatography, 510 (1990) 293–302.

Ehrich et al., Production of C. difficile Antitoxin, Infection and Immunity, Jun. 1980, pp. 1041–1043.

Robert K. Scopes, Separation by Precipitation, Protein Purification (2d edition) pp. 40–45.

Muller et al., Monoclonal Antibodies Specific for C. difficile Toxin B and Their Use in Immunoassays, Jrnl. of Clinical Microbiology, Jun. 1992, pp. 1544–1550.

DiPersio et al., Development of a Rapid Enzyme Immunoassay for C. difficile Toxin A and Its Use in the . . . Disease, Jrnl. of Clinical Micro., Dec. 1991, pp. 2724–2730.

Ryan et al., Rapid Detection of C. difficile Toxin in Human Feces, Jrnl. of Clinical Microbiology, Dec. 1980, pp. 776–779.

Warny et al., Human Antibody Response to C. difficile Toxin A in Relation to Clinical Course of Infection, Infection And Immunity, Feb. 1994, pp. 384–389.

Wolfhagen et al., Toxins A and B of C. difficile, FEMS Microbiology Reviews 13 (1994) 59–64.

O'Shannessy et al., Immobilization of Glycoconjugates by Oligosaccharides: Use of Hydrazido–Derivatized Matrices, Analytical Biochemistry 191, 1–8 (1990).

Lyerly et al., Enzyme–Linked Immunosorbent Assa for C. difficile Toxin A, Jrnl. of Clinical Microbiology, Jan. 1983, pp. 72–78.

Pierce Ordering Catalog, pp. 3–10, (1989).

Domen et al.; Site–Directed Immobilization of Proteins; Jrnl. of Chromatography, 510 (1990) 293–302.

Depitre et al.; Detection of Clostridium difficile Toxins in Stools; Gastroenterol Clin Biol, 1993, 17, 283–286.

Kamiya et al.; Production of Monoclonal Antibody to Clostridium difficile Toxin A . . . Activity; FEMS Microbiology Letters (1991) 311–316.

Katoh et al.; Purification and Some Properties of Cytotoxin Produced by Clostridium difficile; Microbiol. Immunol.; vol. 32 (6), 551–564, 1988.

Ascione et al.; Accuracy in Detection of Clostridium difficile Toxin Direct . . . Colitis; Current Therapeutic Research; vol. 36, No. 5, Nov. 1984.

Grace M. Thorne; Diagnostic Tests in Gastrointestinal Infections; 1994 Current Science ISBN 1–85922–606–X ISSN 0267–1379.

Antibodies, A Laboratory Manual; Harlow, E. et al, Cold Spring Harbor Laboratory; 1988.

Detection of Clostridium difficile toxins in stools.; Depitre, C. et al Gastroenterol Clin. Biol (France) 1993 17(4) pp. 283–286.

Accuracy in detection of Clostridium difficile toxin; Ascione, A; Current Therapeutic Research, vol. 36 #5, Nov. 84, pp. 882–892.

Tresyl activation of a hydroxyalkyl ligand for coupling a hydrazide gel: stable immobilization of T–2 toxin for affinity purification of T–2 antibody; Allam, K; 1987 Anal. Biochem; vol. 162, #1, pp. 171–177.

Diagnostic tests in gastrointestinal infections, Thorne, G. M. 1994, Curr. Opin Gastroenterol vol. 10, 1 (112–118).

Purification and some properties of cytotoxin produced by Clostridium difficile; Katoh. T, Microbiol. Immunol, 1988 32/6 (551–564).

Production of monoclonal antibody to Clostridium difficile toxin A which neutralizes enterotoxicity but not hemagglutination activity; (1991), vol. 81, #3 pp. 311–315, Fems. Microbiol. Lett.

*Primary Examiner*—James C. Housel
*Assistant Examiner*—Ginny Allen Portner
*Attorney, Agent, or Firm*—Thomas, Kayden, Horstemeyer & Risley

[57] ABSTRACT

A method is provided for the purification of *Clostridium difficile* Toxin A comprising reacting impure Toxin A with immobilized mono-specific polyclonal antibodies. The polyclonal antibodies are coupled to a hydrazide group containing matrix such as hydrazide activated agarose gel. The immobilized antibody is specific for Toxin A and will greatly purify Toxin A from a Toxin A containing solution. Antibodies raised to Toxin A purified according to the method are of higher activity than antibodies produced from prior art purified Toxin A.

9 Claims, No Drawings

METHOD OF PURIFICATION OF CLOSTRIDIUM DIFFICILE TOXIN A AND PRODUCTION OF MONO-SPECIFIC ANTIBODIES

FIELD OF THE INVENTION

The invention relates generally to the production and purification of *Clostridium difficile* Toxin A. More particularly, the invention relates to purified Toxin A and its use in preparing antibodies for use in diagnosis of pseudomembranous colitis.

BACKGROUND OF THE INVENTION

*Clostridium difficile* produces an assortment of gastrointestinal diseases in humans and animals ranging from mild diarrhea to life threatening pseudomembranous colitis. It is widely accepted that *C. difficile* causes pseudomembranous colitis in humans as a result of the elimination of the normal flora of the colon by antibiotic usage and subsequent growth of this toxin producing bacterium. The disease usually occurs in hospitalized patients where it causes a massive diarrhea with extensive inflammation of the colon. Mortality rates as high as 44% have been reported. Treatment of the disease is possible but relies on a proper diagnosis which may be accomplished by establishing the presence of the causation organism and demonstrating the characteristic lesions in the colon.

*C. difficile* produces two toxins, designated Toxin A and Toxin B, that are cytotoxic for tissue cultured mammalian cells. In addition to its cytotoxicity, Toxin A also possesses enterotoxin activity. Toxin A causes an accumulation of fluid in the intestine loops and causes extensive damage to the gut mucosa. Although both toxins are typically produced during disease, the principle laboratory diagnostic methods for detection of *C. difficile* have been directed towards detection of Toxin A. For example, a commercial latex test for the presence of Toxin A was marketed by Marion Scientific, a division of Marion Laboratories, Inc. of Kansas City, Mo. This commercial test was, unfortunately, found by subsequent researchers to be non-specific for Toxin A. See Lyerly et al., J. Clin. Micro, 23: 622–623 (1986).

One method for detecting pathogenic *C. difficile* involves the culture of human feces, which requires specialized facilities for long periods of incubation and which has the disadvantage of interference by non-pathogenic *C. difficile* strains. Another method for detecting Toxin B, but which does not work well for detecting Toxin A, is cytotoxicity assays using tissue culture cells. Because Toxin A is a much less potent cytotoxin it is more difficult to detect in tissue culture assays.

Other methods developed for Toxin A detection have been based on the use of specific antibodies to Toxin A. These methods include the enzyme-linked immunosorbent assay (ELISA) as taught by Lyerly et al., J. Clin. Micro., 17: 72–78 (1983) and Laughton et al., J. Infect. Dis., 149: 781–788 (1984). Lyerly et al. reported detection of Toxin A at 1 ng (5 ng/ml) quantities while Laughton et al. reported detection at 0.1 ng (1.0 ng/ml) levels. An ELISA assay using a monoclonal antibody to Toxin A was reported by Lyerly et al., J. Clin. Micro., 21: 12–14 (1985), which could detect 4 ng (0.02 μg/ml) of Toxin A. This detection level is usually adequate to detect the toxin in stool samples from patients with *C. difficile*-related diarrhea. Another antibody dependent test is the Latex Agglutination Test (LAT) wherein antibody is immobilized on latex beads and agglutination of said beads by soluble Toxin A is visualized.

U.S. Pat. No. 4,530,833 to Wilkins et al. teaches a method of purifying Toxin A from cell culture supernatant which comprises an ion-exchange chromatography step followed by isoelectric precipitation. The patent teaches that purified Toxin A is achieved by adjusting the pH and molarity of a solution of impure Toxin A to, preferably, 5.5 and 0.01, respectively. One disadvantage of using isoelectric precipitation for protein purification is that other proteins with similar properties as the desired protein aggregate and coprecipitate with the desired protein to form the isoelectric precipitate. Thus, the precipitate must be washed by resuspension and recentrifugation. This results in loss of the desired protein. In addition, the process prior to and including the precipitation step must be very carefully controlled to control the precipitation step. If the fractions from the ion-exchange column are not carefully and consistently pooled, more or less proteins will co-precipitate with the Toxin A.

Another disadvantage of isoelectric precipitation with respect to purification of Toxin A is that denaturation of Toxin A may result if high speeds are used to pellet the precipitated protein. Thus, the protein will not be active in immunoassays or when used as an immunogen for antibody production. Isoelectric precipitation of proteins may also cause changes in the tertiary structure of the protein. In particular, Toxin A is an extremely hydrophobic protein and its exposure to a low ionic strength buffer for several wash steps can result in its partial denaturation.

Another method of Toxin A purification is taught in U.S. Pat. No. 5,098,826 to Wilkins et al. This method comprises contacting an impure solution of Toxin A with an immobilized reagent containing one or more of the terminal non-reducing structures characteristic of any of the human antigens X, Y, or I. These structures are known to be polysaccharides, and they can be immobilized by binding them to an insoluble matrix, e.g., silica gel, agarose, latex beads, or the like. The Toxin A binds to the immobilized reagent and is then eluted from the reagent in a more pure form. This method requires one of the antigens X, Y, or I, which are relatively expensive to obtain, and thus is an impractical method for purification of useful quantities of Toxin A.

Production of polyclonal antibodies to Toxin A is known in the art. For example, Ehrich et al., Inf. Immun. 28: 1041–43 (1980) teaches a procedure of culturing *C. difficile* and inoculating rabbits to produce polyclonal antibodies to an impure *C. difficile* preparation. Such polyclonal antibodies are not mono-specific for toxin because of the large number of proteins present in culture supernatant. Thus, the performance of toxin specific polyclonal based EIA have been disappointing because of the relatively low toxin specific titer and the high level of nonspecific reactivity of the polyclonal antisera.

Therefore there is a need for a method for the purification of Toxin A as well as a rapid and accurate assay for diagnosis and detection of *C. difficile* Toxin A.

It can be seen by the above that a method for purifying Toxin A which results in a consistently pure and non-denatured protein and which can be used to purify large quantities of protein is needed. Antibodies produced by such a highly purified, active protein will themselves be of higher activity.

SUMMARY OF THE INVENTION

The present invention is drawn to a method for the purification of Toxin A from *Clostridium difficile*. Substantially purified Toxin A is provided which is useful for the production of antibodies to Toxin A. Thus, the invention is also drawn to antibodies, particularly polyclonal antibodies with a high sensitivity for Toxin A. Kits for the diagnosis and detection of *C. difficile* Toxin A are also disclosed.

Additional objects, advantages and novel features of the invention will be set forth in part in the description which follows, and in part will become apparent to those skilled in the art upon examination of the following or may be learned by practice of the invention. The objects and advantages of the invention may be realized and obtained by means of the instrumentalities and combinations particularly pointed out in the appended claims.

DETAILED DESCRIPTION OF A PREFERRED EMBODIMENT

Compositions and methods for the detection of pseudomembranous colitis caused by *C. difficile* are provided. Specifically, a new method for purification and production of Toxin A is disclosed. Further, polyclonal antibodies are provided which are specific for Toxin A of *C. difficile*. The antibodies find use in assays for the detection and diagnosis of *C. difficile*.

DEFINITIONS

The term "substantially pure" or "purified Toxin A" as used herein indicates that the Toxin A preparation is substantially free of contaminating substances when examined by resolving techniques known in the art.

The term "partially pure" or "partially purified Toxin A" refers to Toxin A preparations having some, but not all, contaminants removed.

The term "active Toxin A" refers to Toxin A which gives a positive result on Toxin A assays currently used in the field including ELISA's and the Latex Agglutination Test which uses purified rabbit anti-*C. difficile* antibody immobilized onto Latex beads.

The term "denatured" refers to protein or more specifically, Toxin A, which has lost its native or natural structure or properties.

The term "mono-specific antibody for Toxin A" refers to an antibody which does not have any determinant sites for antigens of *C. difficile* other than Toxin A.

DESCRIPTION

The present invention comprises a highly reproducible method for purifying Toxin A having high activity. The reproducibility of the present process is a very desirable feature of protein purification processes in general and especially for the purification of proteins to be used as antigens. The more pure a preparation of antigen is, the more specific the antibodies produced will be towards that antigen. In addition, reproducibility is of high priority for processes involved in the preparation of products submitted for FDA approval.

Toxin A is produced by *C. difficile* cells which may be cultured as is known in the art. The following references describe the culturing of *C. difficile* and are incorporated herein by reference: Sterne and Wentzel, J. Immun. 65: 175–183 (1950); Ehrich et al., Infect. Immun. 28: 1041–43 (1980); Sullivan et al., Infect. Immun. 35: 1032–40. The present invention comprises reversibly binding the crude or partially purified Toxin A to immobilized polyclonal antibody. Polyclonal antibodies are oxidized and are then bound or immobilized to a hydrazide group containing resin, such as hydrazide activated agarose gel. The resulting immobilized reagent is highly selective for Toxin A and its use as a purification reagent results in a highly purified Toxin A. The purification process is much more reproducible than processes using precipitation because the immuno-affinity step is very selective for Toxin A and the protein product is of consistent composition, namely highly pure and highly active Toxin A. Also, multiple potentially denattiring washing and resuspension steps are not necessary. In addition, the process of selectively binding and eluting Toxin A to the resin does not permanently denature or inactivate the Toxin A. Therefore, more active mono-specific, polyclonal antibodies may be produced by using the purified, highly active, Toxin A of the present invention.

The process of the present invention is more economical than prior art immuno-affinity processes because the immuno-affinity resin is stable and reusable for many uses. The resin materials are fairly inexpensive and the immuno-affinity resin has a high binding capacity because it presents to the Toxin A containing solution two Toxin A binding sites per bound antibody molecule.

The purification method of the present invention involves an immuno-affinity purification. An advantage of the immuno-affinity purification is that the protein is not subjected to centrifugation/rehydration steps during the procedure. The process is thus controlled and very reproducible.

Culture filtrate of *Clostridium difficile* can be applied directly to an immuno-affinity column as described herein. Alternatively, additional steps for purification of the Toxin A prior to application to the immuno-affinity column may be performed. Such steps include high speed centrifugation followed by filtration, precipitation such as ammonium sulfate precipitation, and chromatography such as ion exchange, affinity, or size exclusion chromatography.

The immuno-affinity columns of the present invention utilize hydrazide activated agarose. That is, the antibodies are immobilized onto hydrazide activated agarose through oligosaccharides. Such methods are known in the art. See, e.g., O'Shannessy and Wilchek, Anal. Biochem. 191: 1–8 (1990); Domen et al., J. Chromat., 510: 293–302 (1990); Palmer et al., J. Biol. Chem. 238: 2393 (1963); Schneider et al., J. Bio. Chem. 257: 10766 (1982); all of which references are incorporated by reference herein.

The use of hydrazide group containing resins for biomolecule purification is a known technique. See O'Shannessy and Wilchek supra. Commercial preparations are available wherein agarose beads are provided with spacer arms having terminal hydrazide groups. These hydrazide groups will react with aldehyde groups such as are produced by the oxidation of carbohydrate groups.

Carbohydrate groups are located primarily in the Fc region on antibody molecules. The antigen binding sites are, on the other hand, located on the Fab region of the antibody. Thus, antibodies bound to a hydrazide group containing resin are oriented so that both of their antigen binding sites are presented to antigens such that these immuno-affinity resins may function as better affinity materials. In addition, the long spacer arms of such hydrazide-agarose gels appear to allow for higher binding capacity for antigen, as compared to other types of antibody-resins.

When antibodies elicited to acetate precipitated Toxin A are compared with antibodies elicited to immuno-affinity purified Toxin A, using the purified antibodies immobilized onto latex in the LAT, an average endpoint of approximately 25–35 ng/ml is found with the antibodies from acetate precipitated Toxin A while an average endpoint in the range of about 12.5–25 ng/ml is found for the antibodies from the immuno-affinity purified Toxin A.

The LAT is a more tightly controlled assay than the ELISA and gives more consistent results. The LAT can be carried out as described in U.S. Pat. Nos. 4,879,218 and 5,098,826 to Wilkins et al., and also as described in Lyerly et al., J. Clin. Micro., 21: 12–14 (1985), the disclosures of which are incorporated herein by reference.

Purified Toxin A is useful in studying diseases caused by *C. difficile* and in designing detection tests and treatment plans. In particular, purified Toxin A is necessary for preparing antibodies to Toxin A, which antibodies are used in ELISAs, LATs, and other detection tests such as those described in the above cited references for detecting the presence of Toxin A in biological samples. In the development of any immunoassay, the first consideration is the quality of the antiserum that will be used in the assay. If the antiserum is not sensitive or has cross reactivities with other undesired or related proteins, the assay will not have the desired sensitivity. Thirty (30) or more proteins expressed by *C. difficile* are present in the culture supernatant. Any of these proteins which are present in the final Toxin A product will diminish the efficiency of the product used as an antigen. Therefore, an improved method for purifying large amounts of Toxin A is needed which provides highly pure, nondenatured, Toxin A. An economical production method is needed which is highly specific for Toxin A and which is highly reproducible.

Mono-specific antibodies can be produced in accordance to the present invention by immunizing appropriate animals with Toxin A purified as disclosed herein. It is also anticipated that monoclonal antibodies can be prepared using the Toxin A of the present invention. Mono-specific polyclonal antibodies show high activity in ELISA tests and in the LAT. Antibodies raised against Toxin A of the present invention were up to twice as active in the LAT as antibodies raised against acetate precipitated Toxin A.

In a second embodiment of the invention, polyclonal antibodies can be produced with the purified, highly active Toxin A through methods known in the art. For example, the methods taught by Ehrich et al., Infect. Immun., 28: 1041–43 (1980) and in E. Harlow & D. Lane, *Antibodies-A Laboratory Manual,* Cold Spring Harbor Laboratory (1988), may be used. The initial step is the preparation of a toxoid and immunization of rabbits with the toxoid. Toxin A-adjuvant is then prepared and used for immunization. The collected sera is then purified over protein A.

The above described production and purification of *C. difficile* Toxin A, and its use in preparing antibodies, are illustrated by the following example, which is not intended to be limiting.

EXPERIMENTAL

Protein Purification

*C. difficile* was cultured in 0.85% sodium chloride in dialysis bags suspended in brain-heart infusion (BHI) broth media as generally described by Sterne et al., J. Immun., 65: 175–183 (1950) and Lyerly et al., J. Clin. Micro. 17: 72–78 (1983) (incorporated herein). Five dialysis bags holding 300–500 ml each of 0.85% NaCl were placed in 15L of BHI broth media in a 20L Bellco Spinner flask. Each tube was inoculated with 3 ml of a 18–24 hr culture diluted 1:10 with 0.85% chloride. The cells were cultured anaerobically for about four days at 39° C. ±1° C. After sedimenting the cells by centrifugation at 10,000 RCF for 30 minutes at 2°–8° C., the supernatant was decanted off and clarified by filtration through a 0.45 micron filter.

The culture supernatant was concentrated and washed using an apparatus such as the Minitan Ultrafiltration System with PTHK 100,000 MW packet type ultrafiltration membranes. The supernatant was washed with 50 mM Tris buffer, pH 7.5 containing 0.02% sodium azide using twice the starting volume of the filtered culture supernatant. After washing, the washed culture supernatant was concentrated to approximately 250–300 ml.

The washed and concentrated culture supernatant was next subjected to ion-exchange chromatography. An ion-exchange resin which works well is DEAE-Sepharose. A 300–400 ml column was equilibrated in 50 mM Tris buffer pH, 7.5, 50 mM NaCl, at 2°–8° C. The Toxin A containing solution was loaded onto the column whereupon the Toxin A was retained. Proteins were then eluted using a gradient from 50–250 mM NaCl while the eluant was monitored at 280 nm. Those fractions having an absorbance greater than 0.05 AUFS were subjected to crossed IEP with the fractions run in one dimension and a reference anti-Toxin A antibody in the second dimension. Crude Toxin A fractions were pooled and collected. These fractions can be stored for one week at 2°–8° C. or longer at –20° C.

Immuno-Affinity Column

The immuno-affinity separation column is prepared generally according to the method taught by Pierce Chemical in its 1989 product information brochure on its CarboLink™ Gel. 20 mg of affinity purified anti-Toxin A antibody was oxidized with an equivalent weight amount of sodium meta-periodate by incubating the one to one combination at room temperature for 60 minutes. The mixture was then applied to a 1.6×20 cm Sephadex G-25 column equilibrated and run with 0.1M NaPi, pH 7.0. The eluant was monitored at 280 nm and the protein-containing fractions were pooled.

20 ml hydrazide group containing agarose beads, sold under the trademark "CarboLink" by Pierce Chemical, were washed with the same buffer and then combined with the oxidized antibody. The fixture was incubated 16–18 hours at room temperature and then formed into a small column (2.5×10 cm) where it was washed with the same buffer. The column was monitored at 280 nm to detect uncoupled protein. The column was washed with 5 bed volumes of deionized water followed by 5 bed volumes of 1M NaCl and again with 5 bed volumes of deionized water. The column can be equilibrated and stored in 50 mM Tris, pH 7.5 containing 50 mM NaCl and 0.01% sodium azide.

For use, the immuno-affinity column was equilibrated with about 160 ml 50 mM Tris, pH 7.5. Partially purified Toxin A off the ion-exchange column can be purified over the immuno-affinity separation column as follows. Based on a Bio-Rad protein assay, 75 mg of the crude Toxin A was applied to the column. The column was washed and run with 50 mM Tris, pH 7.5 while monitoring the column eluant at 280 nm until a peak eluted off the column. The column was washed with 100 mM Glycine, pH 2.7 containing 1% Tween 20, while monitoring the observance of the eluant at 280 nm. The purified Toxin A was eluted from the column as one peak and was collected into a container that contained 50 ml of 0.25M Tris, pH 8.0. The protein concentration of the purified Toxin A was measured using a BCA assay. The protein solution was concentrated using an Amicon concentrator such as the Amicon Single Channel Concentrator Model 8050 with a YM 30 membrane to a concentration of 1.2 mg/ml. The purified Toxin A can be stored at –20° C. for up to one year.

Column Regeneration

The immuno-affinity column can be reused up to at least 20 times. After the Toxin A is eluted off the column, the column is washed with 100–150 ml of 1M NaCl followed by 100 ml of 50 mM Tris, pH 7.5. The column is then equilibrated in 50 mM Tris, pH 7.5 containing 0.01% sodium azide and can be stored at 2°–8° C. until ready for reuse.

Toxin A Antibodies

Preparation of antibodies to Toxin A was carded out generally by the method of Ehrich et al., Infect. & Immun. 28, 1041–1043 (1980) (incorporated herein). Due to the toxicity of the purified Toxin A to rabbits, rabbits cannot be immunized initially with the purified Toxin A but rather must be immunized initially with a toxoid of Toxin A. A toxoid is a toxin treated so as to destroy its toxicity but leave it capable of inducing the formation of antibodies on injection. A toxoid was prepared by mixing the Toxin A as purified off the immuno-affinity column with formaldehyde. One ml of 1.2 mg/ml of Toxin A was diluted with 5 ml of sterile saline. One ml of 37% formaldehyde was diluted with 8.25 ml of sterile saline. 6 ml of the prepared 4% formaldehyde solution was added to the diluted Toxin A and the mixture incubated in a 37° C.±2° C. water bath for 18 to 24 hours. The toxoid-Toxin A solution was mixed with an equal volume of Freund's adjuvant and this solution was used to immunize rabbits. Freund's complete adjuvant was used for the first two injections and Freund's incomplete adjuvant used thereafter. An immunization schedule as shown in Table 1 was used for toxoid immunization. A fresh toxoid should be prepared the day before each immunization. Once the emulsion of Toxoid and Freund's adjuvant is prepared, it should be injected within two hours.

TABLE 1

| Immunization Number | Amount (ml) Rabbit | Route: (0.5 ml per Two Sites) | Day of the Schedule |
|---|---|---|---|
| 1 | 1.0 | POP* | 1 |
| 2 | 1.0 | POP | 3 |
| 3 | 1.0 | POP | 8 |
| 4 | 1.0 | POP | 10 |
| 5 | 1.0 | POP | 15 |
| 6 | 1.0 | POP | 17 |
| 7 | 1.0 | POP | 22 |
| 8 | 1.0 | POP | 24 |
| 9 | 1.0 | IM* | 29 |
| 10 | 1.0 | IM | 31 |
| Test Bleed | | | 36 |
| 11 (boost) | 1.0 | IM | 40 |
| Test Bleed | | | 44 |

*POP = popitiel
*IM = intramuscular

On day 36±1,2–3 ml of blood was collected from each rabbit and the anti-Toxin A titer measured using an ELISA assay. An endpoint of greater than or equal to 1:5000 was considered acceptable. If the titer was not acceptable, the rabbits were boosted with another toxoid injection and the titer retested on day 44±1.

Once a protective titer against the toxoid of Toxin A has been achieved, the rabbits can be immunized against the purified Toxin A. The Toxin A was diluted to about 0.4 mg/ml with sterile saline. This solution was then diluted to about 0.2 mg/ml with Freund's incomplete adjuvant. Each rabbit was immunized with 1 ml of this solution. Rabbits were immunized according to the immunization schedule of Table 2.

TABLE 2

| Immunization Number | Amount (ml) Rabbit | Route: (0.5 ml per Two Sites) | Day of the Schedule |
|---|---|---|---|
| 1 | 1.0 | IM | 1 |
| 2 | 1.0 | IM | 8 |
| 3 | 1.0 | IM | 15 |
| 4 | 1.0 | IM | 22 |
| Test Bleed | | | |
| 5 (boost) | 1.0 | IM | 30 |
| Test Bleed | | | 35 |

On approximately the 27th day of the immunization schedule, the animals were tested for antibody titer as described above. If the titer was high enough, at about or higher than 1:40,000, the rabbits were bled and the sera collected.

The sera prepared in the foregoing manner was clarified, when necessary, by high speed centrifugation and/or filtration and then precipitated with 70% ammonium sulfate. The precipitated globulin was resuspended in 20 mM NaPi, pH 7.4 and then purified over a protein A column.

Preparation of Latex-Bound Antibodies

For use in a Latex Agglutination Test the antibodies are bound to latex using the following procedure. Rabbit anti-*C. difficile* Toxin A antibody was prepared and dialyzed into 20 mM NaPi, pH 6.0 with 0.01% sodium azide. The protein concentration of the solution was adjusted to about 2.0 mg/ml. 50 ml of 2.5% (w/v) solids carboxylated polystyrene latex was placed into each of four 250 ml centrifuge bottles. 70 ml of 20 mM NaPi, pH 6.0 was added to each bottle and the bottles centfifuged at 11,000 RCF for 30–40 minutes. The liquid was poured off and the beads were resuspended in 120 ml of the same buffer. (For all latex suspensions, the latex must be resuspended initially in a minimal volume of buffer.) The bottles were centrifuged as before and the washing step was repeated. The beads were then resuspended in 120 ml of the same buffer and 50 mg of 1-ethyl-3-[3-dimethyl aminopropyl]-carbodiimide hydrochloride and 12.5 mg Sulfo-N-hydroxysuccinimide was added to each bottle. The latex suspensions were allowed to incubate for two hours at room temperature while stirring. The suspension was pelleted by centrifugation at 11,000 RCF for 30–40 minutes, the supernatant poured off, and each pellet resuspended in 120 ml of 20 mM NaPi, pH 6.0. The suspension was pelleted as before and this step was repeated. 15 mg of the buffer exchanged antibody was added to each latex suspension and the resulting latex-antibody suspension incubated for 18–20 hours at room temperature while stirring. 2.5 ml of 1M 2-aminoethanol was added to each suspension and the resulting solution incubated for two hours at room temperature while stirring. The latex-antibody was then pelleted at 10,000 RCF for 30–40 minutes, the supernatant decanted and each pellet resuspended in 250 ml of 0.1M glycine-NaOH, pH 8.2 with 0.15M sodium chloride, 0.25% Tween 20, 0.2% sodium azide, and 0.2% BSA. The latex-antibody was pelleted at 10,000 RCF for 30–40 minutes and this step repeated.

LAT

A volume of Toxin A containing solution was mixed with 0.5 ml specimen buffer in a centrifuge tube and vortexed for 30 seconds. The tube was then centrifuged for 15 minutes at a mininum of 1500×g. Using a typical LAT test card, 35 μl of the specimen supernatant was placed in the test circle and 35 μl in the negative circle of the test card. 35 μl of a *C. difficile* culture filtrate was placed in the positive circle. 35 μl of the Toxin A coated latex beads were placed in the test and positive circles. 35 μl of normal rabbit antibody coated latex beads was placed in the negative circle. The contents of each circle were mixed with a separate applicator stick and spread over the surface of each circle. Using a clinical rotator, the test card was rotated for the designated time at 100 rpm. The test was read microscopically under a fluorescent light.

Activity of Antibodies

Table 3 shows the results of a comparison of antibodies raised against acetate precipitated Toxin A with antibodies raised against immuno-affinity purified Toxin A. The Toxin A sample was a sample prepared by acetate precipitation. The antibodies were prepared according to the description recited above. After the rest period, the rabbits were bled every two weeks and the bleeds were purified as described above and coupled to latex beads as described above. The LAT procedure described above was used to compare the antibodies.

As can be seen from the data, antibodies prepared in accordance with the present invention and used in the Latex Agglutination Test gave results of an average endpoint of 12.5–25 ng/ml. Antibodies prepared using acetate precipitation gave results of an average endpoint of 25–35 ng/ml.

TABLE 3

| Antibodies raised against acetate precipitated Toxin A | | | | | | | | |
|---|---|---|---|---|---|---|---|---|
| Toxin A Conc. | Bleed Date 10/3 | | Bleed Date 12/7 | | Bleed Date 2/22 | | Bleed Date 3/22 | |
| (ng/ml) | 2 min. | 4 min. | 2 min. | 4 min. | 2 min. | 4 min. | 2 min. | 4 min. |
| 200 | 3+ | 4+ | 4+ | 4+ | 4+ | 4+ | 4+ | 4+ |
| 100 | 2+ | 3+ | 3+ | 4+ | 2+ | 4+ | 3+ | 4+ |
| 50 | 1+ | 2+ | 2+ | 3+ | 1+ | 3+ | 2+ | 3+ |
| 35 | <1+ | 1+ | 1+ | 2+ | Vague | 1+ | <1+ | 1+ |
| 25 | Neg. | Neg. | Vague | 1+ | Neg. | <1+ | Neg. | Neg. |
| 12.5 | Neg. | Neg. | Neg. | Vague | Neg. | Vague | Neg. | Neg. |
| 6.25 | Neg. | Neg. | Neg. | Neg. | Neg. | Neg. | Neg. | Neg. |

| Antibodies raised against Immuno-affinity purified Toxin A | | | | | | | | |
|---|---|---|---|---|---|---|---|---|
| Toxin A Conc. | Bleed Date 1/4 | | Bleed Date 3/14 | | Bleed Date 4/11 | | Bleed Date 5/24 | |
| (ng/ml) | 2 min. | 4 min. | 2 min. | 4 min. | 2 min. | 4 min. | 2 min. | 4 min. |
| 200 | 4+ | 4+ | 4+ | 4+ | 4+ | 4+ | 4+ | 4+ |
| 100 | 4+ | 4+ | 4+ | 4+ | 4+ | 4+ | 3+ | 4+ |
| 50 | 4+ | 4+ | 3+ | 4+ | 3+ | 4+ | Vague | 2+ |
| 35 | 3+ | 4– | 1+ | 3+ | Vague | 3+ | <1+ | 1+ |
| 25 | 1 | 2+ | Vague | 1+ | Neg. | <1+ | Neg. | Neg. |
| 12.5 | Vague | 1+ | Neg. | Vague | Neg. | Neg. | Neg. | Neg. |
| 6.25 | Neg. | <1+ | Neg. | Neg. | Neg. | Neg. | Neg. | Neg. |

The foregoing description of preferred embodiments of the invention has been presented for purposes of illustration and description. It is not intended to be exhaustive or to limit the invention to the precise forms disclosed, and obviously many modifications and variations are possible in light of the above teaching. It is intended that the scope of the invention be defined by the claims appended hereto.

What is claimed is:

1. A method of purifying *Clostridium difficile* Toxin A, comprising:

coupling Toxin A antibodies to a hydrazide group containing matrix;

contacting a solution containing Toxin A with said matrix so that said Toxin A is selectively retained on said coupled antibody matrix; and eluting purified Toxin A from said antibody matrix wherein the elution buffer comprises Tween 20.

2. The method of claim 1, wherein said antibodies are polyclonal antibodies produced from a rabbit.

3. The method of claim 2, wherein said polyclonal antibodies are purified with protein A.

4. The method of claim 1, wherein said antibodies are oxidized with sodium meta-periodate.

5. The method of claim 1, wherein said matrix is hydrazide activated agarose beads.

6. The method of claim 1, wherein said coupled antibody matrix is formed into a column.

7. A method of purifying *Clostridium difficile* Toxin A, comprising;

culturing *Clostridium difficile* cells;

separating the supernatant from the solids of said cell culture;

partially purifying said supernatant over an ion-exchange column to result in a Toxin A enhanced solution; and purifying said partially purified Toxin A containing solution over an immuno-affinity column, said column comprising anti-Toxin A antibodies coupled to a hydrazide group containing matrix wherein said Toxin A is eluted from said immuno-affinity column in a buffer comprising Tween 20.

8. *Clostridium difficile* Toxin A, prepared by the method of claim 1.

9. *Clostridium difficile* Toxin A, purified by selectively retaining Toxin A from a Toxin A containing solution on a hydrazide group containing resin and selectively eluting purified Toxin A from said resin wherein the elution buffer comprises Tween 20.

* * * * *